United States Patent [19]
Ueoka et al.

[11] Patent Number: 6,002,054
[45] Date of Patent: Dec. 14, 1999

[54] METHOD FOR PRODUCING ALCOHOL

[75] Inventors: Hideaki Ueoka; Futoshi Nishigaki; Osamu Tabata, all of Wakayama, Japan

[73] Assignee: Kao Corporation, Tokyo, Japan

[21] Appl. No.: 08/973,743

[22] PCT Filed: Jun. 12, 1996

[86] PCT No.: PCT/JP96/01601

§ 371 Date: Dec. 22, 1997

§ 102(e) Date: Dec. 22, 1997

[87] PCT Pub. No.: WO97/00841

PCT Pub. Date: Jan. 9, 1997

[30] Foreign Application Priority Data

Jun. 20, 1995 [JP] Japan .................................. 7-178233

[51] Int. Cl.$^6$ .................................................. C07C 29/149
[52] U.S. Cl. .......................................... 568/885; 568/814
[58] Field of Search ..................... 568/814, 817, 568/853, 864, 877, 885; 562/606

[56] References Cited

U.S. PATENT DOCUMENTS 4,413,063  11/1983  Audibert et al. ....................... 518/700
5,233,099   8/1993  Tabata et al. ......................... 568/885

*Primary Examiner*—Gary Geist
*Assistant Examiner*—Sreeni Padmanabhan
*Attorney, Agent, or Firm*—Oblon, Spivak, McClelland, Maier & Neustadt, P.C.

[57] ABSTRACT

A method for producing an alcohol comprising the steps of continuously feeding starting materials of an alcohol; and carrying out catalytic reduction reaction of the starting materials in the presence of a hydrogenation catalyst, wherein said starting materials of an alcohol and a hydrogen gas are fed in a gaseous state or a mixture of liquid and gaseous states in a reduction reactor, and wherein said catalytic reduction reaction of the starting materials is carried out under temperature conditions, pressure conditions, and conditions of a molar ratio of hydrogen ((hydrogen molecules/(acyl groups in the starting materials)), sufficient to give an evaporation ratio of the starting materials of from 20 to 80% by weight, and wherein a ratio of VG to VL satisfies the following relationship in the reduction reactor: $100 \leq VG/VL \leq 10000$, wherein "VG" stands for the superficial velocity at a gas phase portion of a mixture of the starting materials of an alcohol fed and hydrogen gas; and "VL" stands for the superficial velocity at a liquid phase portion of the mixture.

7 Claims, 2 Drawing Sheets

METHOD FOR PRODUCING ALCOHOL

This is the US National Stage Application of PCT/JP96/01601 filed Jun. 12, 1996 now WO 97/00841 published Jan. 9, 1997.

TECHNICAL FIELD

The present invention relates to an improved method for producing an alcohol comprising the steps of continuously feeding starting materials of an alcohol in the presence of a hydrogenation catalyst and carrying out catalytic reduction reaction to give an alcohol.

More specifically, the present invention relates to a method for producing an alcohol wherein the amounts of components which are normally contained in the product alcohols, such as unreacted starting materials of alcohols, wax esters formed as reaction intermediates, and hydrocarbons formed as by-products are remarkably lowered to such an extent that a purification step, such as distillation, is not necessitated, thereby notably improving the yield of an alcohol. Moreover, it relates to a method for producing an alcohol wherein the amounts of the hydrocarbons formed as by-products are lowered and particular wax esters formed as reaction intermediates are selectively kept in the reaction system, so that separation, recovery, and recycle in subsequent processes are made easy, thereby making necessary amounts of hydrogen low, and thus making it highly economically advantageous.

BACKGROUND ART

Methods for producing alcohols comprising carrying out reduction reaction of starting materials of an alcohol, such as a fatty acid ester, a fatty acid triglyceride, and a fatty acid, in the presence of a hydrogenation catalyst have been already known in the field of art. The reduction reaction is generally carried out under conditions of a pressure of from 200 to 300 atm. and a temperature of from 200 to 300° C. In view of carrying out such methods in an actual production plant, however, a process at such a high pressure requires not only equipments with sufficient pressure resistance but also sufficient maintenance of the equipments for keeping airtightness and the like. Such equipments would require high equipment investments and high running costs.

In order to overcome these problems and produce alcohols at lower costs, various studies have been recently made on hydrogenation reaction at a relatively low pressure. The results of the studies are disclosed in, for example, Japanese Patent Examined Publication No. 4-72810, Japanese Patent Laid-Open No. 64-47726, Japanese Patent Unexamined Publication No. 4-504408 and Japanese Patent Examined Publication No. 4-57655.

Japanese Patent Examined Publication No. 4-72810 discloses a method for producing a fatty acid alcohol comprising hydrogenating a fatty acid having a number of carbon atoms corresponding to the resulting alcohol, or an ester thereof at a reaction pressure of from 20 to 100 bar and a reaction temperature of from 150 to 300° C. Similarly, Japanese Patent Laid-Open No. 64-47726 discloses a method for hydrogenating a fatty acid methyl ester in a molar ratio of hydrogen to ester of from 10:1 to 500:1 at a reaction pressure of from 20 to 100 bar and a reaction temperature of 160 to 270° C.

Under the above-mentioned conditions, a fatty acid or an ester thereof remaining as unreacted starting materials and a wax ester formed as a reaction intermediate are included in the resulting alcohol at the outlet of the reactor, and hence, the yield of alcohol is liable to be lowered. The reasons for a low yield of alcohol are as follows: In the hydrogenation reaction, the amount of hydrogen dissolved in a liquid phase comprising a fatty acid or an ester thereof in the reaction system is decreased as the reaction pressure is decreased, thereby drastically lowering the reaction activity. In addition, the chemical reaction for producing an alcohol is an equilibrium reaction, and the equilibrium shifts to the side where a wax ester formed as the reaction intermediate remains in the resulting alcohol at the given pressure conditions mentioned above. Furthermore, the resulting alcohol is also reduced to hydrocarbons under the above-mentioned conditions, which leads to a further decrease in the yield of the alcohol. Additionally, in the case where a fatty acid having 8 to 18 carbon atoms or an ester thereof is hydrogenated under the above-mentioned conditions, the boiling point region of a hydrocarbon formed as a by-product overlaps with that of a short chain aliphatic alcohol, and hence, it is difficult to separate the hydrocarbons from the alcohol in the subsequent processes by distillation. Accordingly, in order to carry out hydrogenation reaction under the above-mentioned conditions, it is necessary to separate a short chain fraction from a long chain fraction in a fatty acid or an ester thereof before the hydrogenation reaction.

Japanese Patent Unexamined Publication No. 4-504408 discloses a method for producing an aliphatic alcohol comprising hydrogenating in a gas phase reaction a lower alkyl ester of a fatty acid under the conditions of a reaction pressure of from 5 to 100 bar, a reaction temperature of from 140 to 240° C., and a molar ratio of hydrogen molecules to ester of from 200:1 to 2000:1, wherein a mixed material of the ester and hydrogen molecules is brought into contact with a hydrogenation catalyst at a temperature constantly kept higher than its dew point.

By conducting the hydrogenation reaction in the gas phase under the above-mentioned conditions, the conventional problem regarding the amount of hydrogen molecules dissolved in the liquid phase at a low pressure can be solved, and thereby the reaction activity is remarkably improved. In addition, since the reaction equilibrium in the production of alcohols largely shifts toward the formation of alcohols in the gas phase, the amounts of esters remaining as the unreacted starting materials and a wax ester formed as the reaction intermediate included in the resulting alcohols at the outlet of the reactor can be expected to be decreased. Actually, however, a side reaction, namely, the reduction reaction of the alcohols to hydrocarbons, is also accelerated, which results in excellent reactivity but poor selectivity, and hence, the yield is rather notably decreased. Furthermore, in the gas phase reaction, the ester used as the starting materials is diluted with a large amount of a hydrogen gas and then fed to a catalytic layer in the form of vapor. As a result, when the amount of the starting materials fed per unit time is made large, namely, when the productivity is to be increased, the flow rate of the vapor within the reactor becomes high to such an extent that the ester can disadvantageously flow through the catalytic layer without being subjected to catalytic reduction reaction. The unreacted starting material ester included in the resulting alcohol has a boiling point region substantially the same as that of the alcohol having a corresponding number of carbon atoms, thereby making it difficult to separate by distillation. In order to overcome this problem, in Japanese Patent Unexamined Publication No. 4-504408, the unreacted starting material ester is first converted to a wax ester in the subsequent process of transesterification, and then the wax ester is separated from the obtained alcohol by distillation. However, such an additional process give rise to higher overall costs.

In the hydrogenation reaction utilizing a gas phase reaction disclosed in Japanese Patent Unexamined Publication No. 4-504408 and Japanese Patent Examined Publication No. 4-57655, since a mixed material of an ester and hydrogen to be brought in contact with a hydrogenation catalyst is always kept at a temperature higher than its dew point, the reaction temperature and pressure, the molar ratio of hydrogen and the kinds of starting materials to be used are considerably restricted. For example, the use of a naturally occurring fatty acid ester, fatty acid triglyceride or fatty acid having short and long chain moieties with 8 to 18 carbon atoms is not practical in view of the necessary amount of hydrogen and the size of equipments.

DISCLOSURE OF THE INVENTION

Accordingly, one object of the present invention is to provide a method for producing an alcohol comprising carrying out catalytic reduction reaction of starting materials of an alcohol in the presence of a hydrogenation catalyst, wherein the method is carried out without having a step of separating the starting materials depending upon the chain length before the reduction reaction, and having excellent reactivity and selectivity even at a low reaction pressure; and specifically, to provide a method for producing an alcohol wherein the amounts of the starting materials of an alcohol remaining unreacted, the wax ester formed as a reaction intermediate, and the hydrocarbons formed as by-products included in the resulting alcohol are lowered to such an extent that a purification process such as distillation is not needed, and thereby having a high yield of the alcohol.

Another object of the present invention is to provide a method for producing an alcohol comprising carrying out catalytic reduction reaction of the stating materials of an alcohol in the presence of a hydrogenation catalyst, wherein the amount of hydrocarbons formed as by-products can be lowered even at a low reaction pressure and the amount of the starting materials of an alcohol remaining unreacted in the resulting alcohol can be lowered to a minimal extent as possible, and an wax ester formed as a reaction intermediate is allowed to selectively remain in the resulting alcohol, so that separation, recovery, and recycle in subsequent processes are made easy, thereby making necessary amounts of hydrogen low, and thus making it highly economically advantageous.

In order to solve the above problems in a method for producing an alcohol comprising carrying out catalytic reduction reaction of starting materials of an alcohol, such as a fatty acid ester, a fatty acid triglyceride, or a fatty acid, in the presence of a hydrogenation catalyst, the present inventors have conducted intensive studies concerning the reaction conditions and found that the amount of a wax ester or a hydrocarbon can be remarkably lowered by carrying out catalytic reduction of the starting materials of an alcohol under the temperature conditions, the pressure conditions, and the molar ratios of hydrogen, sufficient to give an evaporation ratio of the starting materials of an alcohol of less than 100% by weight, particularly from 20 to 80% by weight. The present invention is completed based upon this finding.

Specifically, the present invention is concerned with the following:

(1) A method for producing an alcohol comprising the steps of:

continuously feeding starting materials of an alcohol; and carrying out catalytic reduction reaction of the starting materials in the presence of a hydrogenation catalyst, wherein the starting materials of an alcohol and a hydrogen gas are fed in a gaseous state or a mixture of liquid and gaseous states in a reduction reactor, and wherein the catalytic reduction reaction of the starting materials is carried out under temperature conditions, pressure conditions, and conditions of a molar ratio of hydrogen ((hydrogen molecules)/(acyl groups in the starting materials)), sufficient to give an evaporation ratio of the starting materials of from 20 to 80% by weight;

(2) The method described in item (1) above, wherein a ratio of VG to VL satisfies the following relationship in the reduction reactor:

$$100 \leq VG/VL \leq 10000,$$

wherein "VG" stands for a superficial velocity at a gas phase portion of a mixture of the starting materials of an alcohol fed and a hydrogen gas; and "VL" stands for a superficial velocity at a liquid phase portion of the mixture;

(3) The method described in item (1) or (2) above, wherein the starting materials of an alcohol are a fatty acid ester or a fatty acid;

(4) The method described in item (3) above, wherein the fatty acid ester or the fatty acid is derived from coconut oil, palm oil, or palm kernel oil;

(5) The method described in any one of items (1) to (4), wherein the evaporation ratio of the starting materials of an alcohol is 20% by weight or more and less than 60% by weight in the reduction reaction;

(6) The method described in any one of items (1) to (4), wherein the evaporation ratio of the starting materials of an alcohol is from 60 to 80% by weight in the reduction reaction;

(7) The method described in any one of items (1) to (6), wherein a fixed bed reactor containing a hydrogenation catalyst fixed inside the reactor is used as the reduction reactor; and (8) The method described in any one of items (1) to (7), wherein the temperature inside the reduction reactor is from 100 to 300° C., and the pressure inside the reduction reactor is from 10 to 100 atm.

BEST MODE FOR CARRYING OUT THE INVENTION

Figure 1:
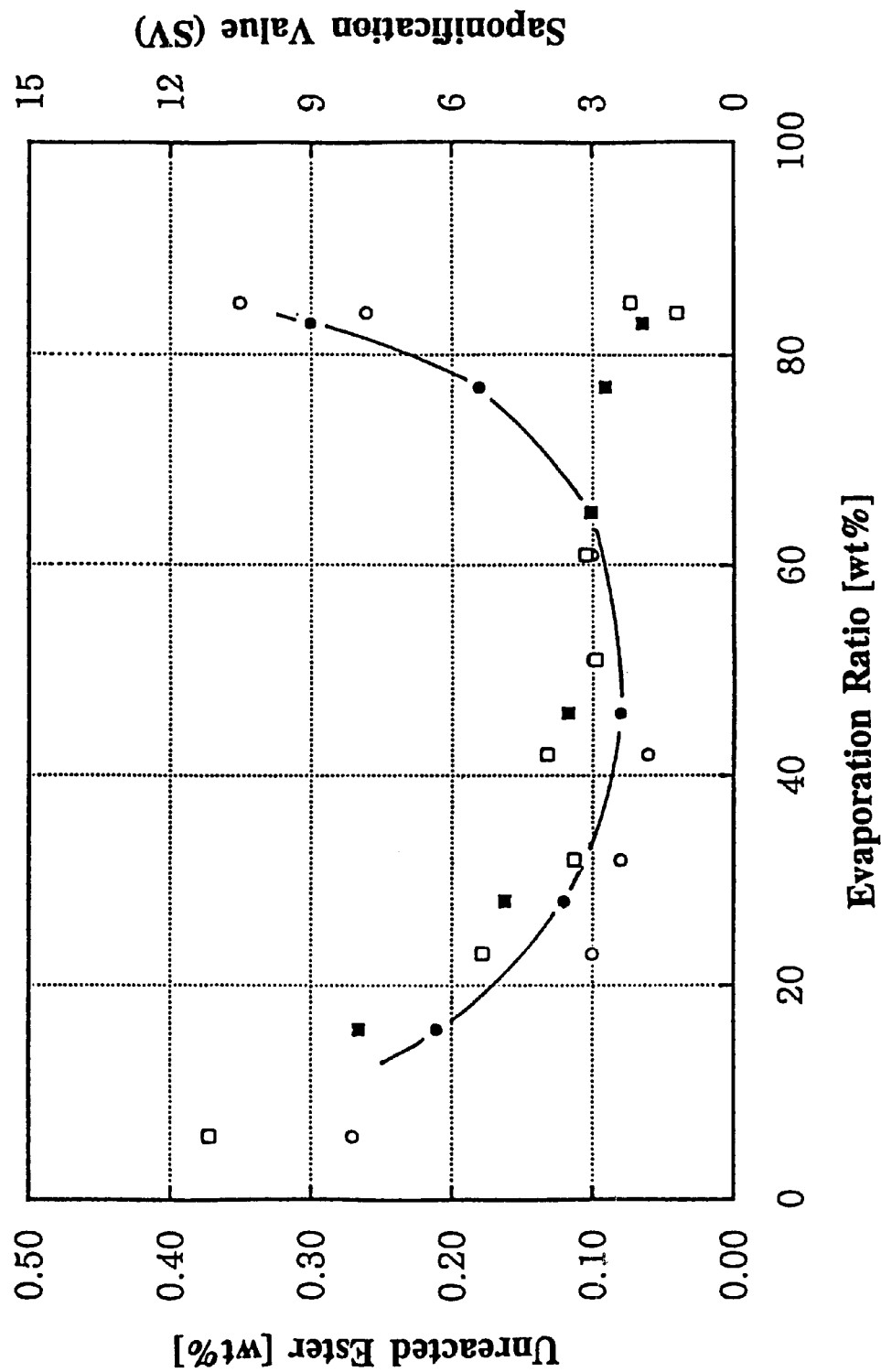
FIG. 1 is a graph showing the relationship between the evaporation ratio of the starting materials of an alcohol and qualities of the resulting products, such as amounts of unreacted ester and saponification values, wherein □ and ■ indicate saponification values; and ○ and ● indicate the amounts of unreacted esters. Here, ■ and ● are data obtained under the conditions of 50 atm. and 220° C.

In the present invention, the starting materials of an alcohol fed in the hydrogenation reaction include fatty acid esters or fatty acids. Also, fatty acid triglycerides may be used. The fatty acid esters or fatty acids mentioned above may be preferably derived from coconut oil, palm oil, or palm kernel oil from the viewpoint of easy availability.

The fatty acid esters used as the starting materials of an alcohol are not particularly limited, and examples thereof include fatty acid esters each comprising an alcohol moiety with one or more carbon atoms and a fatty acid moiety which is saturated or unsaturated, linear or branched moiety, wherein one or more ester bonds are contained in the ester molecule. Further, alicyclic carboxylic acid esters and aromatic carboxylic acid esters may also be used.

The alcohol moiety of the above-mentioned esters is not particularly limited, and the examples include methanol, ethanol, 1-propanol, 2-propanol, 1-butanol, 2-butanol, 2-ethylhexanol, 2,2-dimethyl-1,3-propanediol, ethylene glycol, propylene glycol, 1,4-butanediol, 1,6-hexanediol, 1,10-decanediol, cyclohexanol, benzyl alcohol, diethylene glycol, glycerol, trimethylolpropane and the like.

The fatty acid moiety of the above-mentioned esters is not particularly limited, and the examples include formic acid, acetic acid, caproic acid, caprylic acid, capric acid, lauric acid, myristic acid, palmitic acid, stearic acid, isostearic acid, oleic acid, oxalic acid, maleic acid, adipic acid, sebacic acid, cyclohexanecarboxylic acid, benzoic acid, phthalic acid and the like.

Examples of the fatty acid esters mentioned above include methyl caproate, methyl caprylate, methyl caprate, methyl laurate, methyl myristate, methyl palmitate, methyl stearate, ethyl caproate, ethyl caprylate, ethyl caprate, ethyl laurate, ethyl myristate, ethyl palmitate, ethyl stearate, and the like.

Examples of fatty acid triglycerides include known natural fats and oils, such as coconut oil, palm oil, palm kernel oil, soybean oil, rapeseed oil, cotton seed oil, olive oil, beef tallow, fish oil, and the like. Among them, fatty acid triglycerides derived from coconut oil, palm oil, and palm kernel oil are preferably used. These fatty acid triglycerides may be used singly or in combination with two or more kinds.

The fatty acids to be contained in the starting materials of an alcohol are not particularly limited and the same ones listed as those constituting the above-mentioned fatty acid esters and fatty acid triglycerides may be used. Examples thereof include formic acid, acetic acid, caproic acid, caprylic acid, capric acid, lauric acid, myristic acid, palmitic acid, stearic acid, isostearic acid, oleic acid, oxalic acid, maleic acid, adipic acid, sebacic acid, cyclohexanecarboxylic acid, benzoic acid, phthalic acid and the like, with a preference given to capric acid, lauric acid, myristic acid, palmitic acid, and stearic acid. Particularly, fatty acids derived from coconut oil, palm oil, or palm kernel oil, the fatty acids containing lauric acid, are preferred because of their availability. These fatty acid esters, fatty acid triglycerides, or fatty acids may be used singly or in combination of two or more kinds.

Accordingly, in the present invention, the fatty acid to be contained in the starting material mixture is preferably one derived from coconut oil, palm oil or palm kernel oil.

The hydrogenation catalyst used in the present invention is not particularly limited and any catalysts known in the art used for hydrogenation may be used. Examples thereof include the copper-containing hydrogenation catalysts, such as Cu—Cr, Cu—Zn, Cu—Si, Cu—Fe—Al, Cu—Zn—Ti and the like. The shapes of the catalyst are not particularly limited, which may be suitably selected from powdery, granular, tablet or other forms, depending on the types of the reactors.

Next, the method for producing an alcohol of the present invention will be illustrated specifically.

In the present invention, alcohols are produced by the catalytic reduction reaction, which is a known method. The reactors used in the present invention are not particularly limited as long as they are devices capable of continuously feeding the mixture of the starting materials of an alcohol and a hydrogen gas. Examples thereof include a fluidized bed reactor wherein the catalytic reaction is carried out with a fluidized catalyst; a moving bed reactor wherein the catalytic reaction is carried out by feeding a fluid while a catalytic bed as a whole is gradually dropped by gravity; and a fixed bed reactor wherein the catalytic reaction is carried out by feeding a fluid so that it contacts with a fixed catalyst. In the present invention, in order to smoothly proceed the reaction in the gas phase, the fixed bed reactor is preferably used.

The starting materials of an alcohol to be fed to the reduction reactor is pre-heated and vaporized by a known method utilizing a packed column or the like. At this point, not all the starting materials of an alcohol are needed to be vaporized. In other words, it is possible to feed the starting materials of an alcohol, a part of which is vaporized depending upon the reaction conditions in the reduction reactor.

In the present invention, all or a part of the starting materials of an alcohol are vaporized, and the starting materials of an alcohol and a hydrogen gas are fed to the reduction reactor in a gaseous state or a mixture of liquid and gaseous states, wherein the catalytic reduction of the starting materials of an alcohol is carried out under temperature conditions, pressure conditions, and conditions of a molar ratio of hydrogen, sufficient to give an evaporation ratio of the starting materials of an alcohol of from 20 to 80% by weight, and more preferably 30 to 75% by weight. By the adjustment of the reaction conditions mentioned above, an atmosphere including the starting materials of an alcohol in the form of a liquid and a gas and a hydrogen gas is provided in the reduction reactor. Thus, it is possible to prevent the lowering in the selectivity which otherwise occurs in the conventional reaction consisting of the gas phase reaction alone, namely, to largely decrease the amount of the hydrocarbons formed by the reduction reaction of an alcohol.

The present invention utilizes the property that the chemical reaction for producing an alcohol is an equilibrium reaction, and the equilibrium can shift toward a product side in a gas phase reaction, that is, the equilibrium shifts toward the alcohol side, in this case. Specifically, the reaction activity can be improved by vaporizing a part of the starting materials of an alcohol and carrying out both liquid phase reaction and gas phase reaction in the reduction reactor, so that the amount of the unreacted starting materials included in the resulting alcohol can be lowered. In addition, the amount of the wax ester formed as the reaction intermediate can be decreased by utilizing the reaction equilibrium in the gas phase reaction. Furthermore, in this case, since the alcohol formed in the liquid phase is transformed into a gas phase, the reaction equilibrium in the liquid phase can be further shifted toward the formation of an alcohol. In this manner, the amount of the wax ester formed as the reaction intermediate can be further decreased as compared with that in the conventional methods for producing alcohols at low pressures.

Such a phenomenon regarding the shifting of the reaction equilibrium owing to the presence of both a gas phase and a liquid phase is also disclosed by Hanika et al. (J. Hanika, B. N. Lukjanov, V. A. Kirillov and V. Stanek, "HYDROGENATION OF 1,5-CYCLOOCTADIENE IN A TRICKLE BED REACTOR ACCOMPANIED BY PHASE TRANSITION", Chem. Eng. Commun. 40, 183 (1986)).

Also, the reaction equilibrium in the production of an alcohol is disclosed by Muttzall et al. (K. M. K. Muttzall and P. J. v. d. Berg, Chem. React. Engng. Proceedings of the 4th European Symposium, 1968, p. 277, Pergamon Press, 1971).

Accordingly, the reaction conditions of the present invention are not particularly limited as long as the reduction reaction is carried out under temperature conditions, pressure conditions, and conditions of a molar ratio of hydrogen, sufficient to give an evaporation ratio of the starting materials of an alcohol of from 20 to 80% by weight, namely, as long as the reduction reaction is carried out in an atmosphere including the starting materials of an alcohol in the form of liquid and gaseous states and a hydrogen gas.

The evaporation ratio of the starting materials of an alcohol can be obtained by using a known a high-pressure gas-liquid equilibrium calculation expression such as Soave-Redlich-Kwong (SRK) expression given below.

$$\phi i^V Yi\pi = \phi i^L Xi\pi$$

$$\ln \phi i = \frac{1}{RT} \int_v^\infty \left[ \left( \frac{\partial P}{\partial Ni} \right)_{T,V,Nj(j \neq i)} - \frac{RT}{V} \right] dV - \ln Z$$

$$P = \frac{RT}{V-b} - \frac{a(T)}{V(V+b)}$$

wherein
$\phi i^V$: Fugacity coefficient of component "i" in the gas phase;
$\phi i^L$: Fugacity coefficient of component "i" in the liquid phase;
Xi: Composition of component "i" in the liquid phase;
Yi: Composition of component "i" in the gas phase;
P: Pressure;
V: Volume;
T: Temperature;
Z: Compressibility factor;
a(T), b: Constants; and
R: Gas constant.

The reaction equilibrium state can be calculated, for instance, by using an expression of Muttzall et al. (K. M. K. Muttzall and P. J. v. d. Berg, Chem. React. Engng. Proceedings of the 4th European Symposium, 1968, p. 277, Pergamon Press, 1971).

$$R—COOCH_2R + 2H_2 \leftrightarrows 2RCH_2OH$$

wherein the equilibrium constant k is represented as follows:

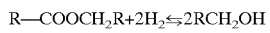

$$k = 9.65 \times 10^{-8} \exp(4900/T)$$

In preferred reaction conditions of the present invention, the ratio of VG/VL satisfies the relationship of:
preferably $100 \leq VG/VL \leq 10000$,
more preferably $100 \leq VG/VL \leq 8000$, and
most preferably $200 \leq VG/VL \leq 6000$
in the reduction reactor, wherein "VG" stands for a superficial velocity at a gas phase portion of the mixture of the starting materials of an alcohol and a hydrogen gas; and "VL" stands for a superficial velocity at a liquid phase portion of the mixture.

Here, the term "superficial velocity at the liquid phase portion" is calculated by dividing a volume flow rate of the starting materials of an alcohol by the cross section of the reactor, wherein the starting materials of an alcohol are present in the form of a liquid without being evaporated the reduction reactor, and the term "superficial velocity at the gas phase portion" is calculated by dividing a volume flow rate of the mixture of the starting materials of an alcohol and a hydrogen gas in the reduction reactor by the cross section of the reactor, the mixture being in the form of a gas phase.

The ratio of the superficial velocity (VG) at the gas phase portion to the superficial velocity (VL) at the liquid phase portion in the reduction reactor is preferably 10000 or less for the following reasons: When the velocity ratio exceeds 10000, the velocity at the gas phase portion becomes notably larger than that at the liquid phase portion, and hence, the starting materials of an alcohol being present in the gas phase portion cannot have sufficient catalytic effects with the hydrogenation catalyst. As a result, a large amount of the unreacted starting materials remains in the resulting alcohol.

Also, the velocity ratio is preferably 100 or more for the following reasons: When the velocity ratio is smaller than 100, the residence time in the catalytic layer at the liquid phase portion becomes short, and hence, the starting materials of an alcohol in the liquid phase portion cannot have sufficient catalytic effects with the hydrogenation catalyst. As a result, a large amount of the unreacted starting materials remains in the resulting alcohol.

The preferred embodiments of the present invention in view of the evaporation ratio of the starting materials of an alcohol will now be described.

In one preferred embodiment of the present invention, for the purpose of producing an alcohol with high purity, the reaction conditions are determined, sufficient to give an evaporation ratio of the starting materials of an alcohol of from 60 to 80% by weight, more preferably from 60 to 75% by weight, and most preferably from 60 to 70% by weight during the reduction reaction. In the present specification, the term "evaporation ratio" means a weight percentage of the amount of the starting materials of an alcohol being vaporized in the entire starting materials of an alcohol.

In this embodiment, the conditions are satisfactorily met, sufficient to give an evaporation ratio of the starting materials of an alcohol of preferably 60% by weight or more for the following reasons: The present invention utilizes the property that the chemical reaction for the production of alcohol is an equilibrium reaction, and the equilibrium can shift toward the product side in the gas phase reaction, i.e., the equilibrium shifts toward an alcohol side. Therefore, lower the evaporation ratio of the starting materials of an alcohol becomes, smaller the proportion of the gas phase reaction is, so that the equilibrium is less liable to shift toward the alcohol side, thereby resulting in an increase in the amount of the wax ester formed as the reaction intermediate. When the conditions are so achieved, sufficient to give an evaporation ratio of 60% by weight or more, however, the above equilibrium shift can be effectively performed, so that it is possible to obtain an alcohol with high quality having a further lowered amount of the wax ester remaining therein.

Also, in this embodiment, the evaporation ratio of the starting materials of an alcohol is preferably 80% by weight or less for the following reasons:

When the conditions are satisfactorily met, sufficient to give an evaporation ratio exceeding 80% by weight, the amount of the wax ester formed as the reaction intermediate during reaction owing to the effects of the gas phase reaction can be decreased. Nevertheless, a larger amount of a hydrogen gas is necessary during reaction for the vaporization of the starting materials of an alcohol, which in turn can lead to a large scale of the reduction reactor and other equipments such as pipe arrangements. Furthermore, since the flow rate of the vapor of the starting materials of an alcohol through the catalytic layer is high, the unreacted starting materials flow through the catalytic layer without being subjected to reduction reaction, thereby making it difficult to separate the unreacted starting materials from the resulting alcohol.

When the conditions are satisfactorily met, sufficient to give an evaporation ratio of 80% by weight or less, however, the necessary amount of a hydrogen gas in the reaction can be notably lowered, thereby resulting in a smaller scale of the equipments. In addition, since the flow rate of the vapor of the starting materials of an alcohol through the catalytic layer can be made low, the unreacted starting materials are prevented from flowing through the catalytic layer without being subjected to reduction reaction.

The term "wax ester" herein means a fatty acid ester having a comparatively large molecular weight formed by esterification or transesterification between the alcohol produced during the hydrogenation reaction and the starting materials of an alcohol. The wax ester can be further subjected to hydrogenation reaction depending upon the reaction conditions, which can in turn be changed into an alcohol.

In order to achieve the evaporation ratio of the starting materials of an alcohol in the gas phase within the above-mentioned range, the reaction conditions such as a temperature, a pressure and a molar ratio of hydrogen are suitably adjusted as follows:

As for the temperature and pressure conditions, they may more preferably satisfy a temperature inside the reduction reactor in the range of from 100 to 300° C. and a pressure inside the reduction reactor in the range of from 10 and 100 atm. Particularly suitable pressure and temperature condition ranges are a pressure of from 20 to 60 atm. and a temperature of from 150 to 270° C. A pressure of 10 atm. or more is preferred from the viewpoint of keeping the reaction speed and shifting the reaction equilibrium toward the product side. A pressure of 100 atm. or less is preferred from the viewpoint of easily vaporizing the starting materials of an alcohol at this pressure and preventing increase in costs for the equipments and in the maintenance costs owing to higher pressures. In addition, a temperature of 100° C. or more is preferred from the viewpoint of keeping the reaction speed and easily vaporizing the starting materials of an alcohol, and a temperature of 300° C. or less is preferred from the viewpoint of the selectivity of the resulting alcohol.

The term "molar ratio of hydrogen" in the present specification means a numeral value expressed by (hydrogen molecules)/(acyl groups in the starting materials of an alcohol) in the reactor.

In the case where a mixture of fatty acid methyl esters listed in Table 1, for example, is used as the starting materials of an alcohol, the molar ratio of hydrogen is preferably in the range of from 100 to 1000, and more preferably in the range of from 200 to 800. A molar ratio of hydrogen of 100 or more is preferred from the viewpoint of achieving a desired evaporation ratio without largely raising the reaction temperature, and a molar ratio of 1000 or less is preferred from the viewpoint of the restriction in the scale of the equipments. Alternatively, in the case where lauric acid, for example, is used as a starting material of an alcohol, the molar ratio of hydrogen is preferably in the range of from 20 to 800, and more preferably in the range of from 50 to 700.

TABLE 1

| Kinds of Esters | Parts by weight |
| --- | --- |
| Methyl Caprylate | 4.6 |
| Methyl Caprate | 4.1 |
| Methyl Laurate | 50.9 |
| Methyl Myristate | 16.0 |

TABLE 1-continued

| Kinds of Esters | Parts by weight |
| --- | --- |
| Methyl Palmitate | 7.6 |
| Methyl Stearate | 16.8 |

By the adjustment of the reaction conditions within the above-mentioned ranges, it is possible to obtain an alcohol wherein the amounts of the unreacted starting materials of an alcohol, the wax ester and the hydrocarbons are remarkably lowered to such an extent that a purification step is not necessitated.

In another preferred embodiment of the present invention, for the purpose of industrially advantageously producing an alcohol, the reaction conditions are determined, sufficient to give an evaporation ratio of the starting materials of an alcohol of 20% by weight or more and less than 60% by weight, more preferably 30% by weight or more and less than 60% by weight, and most preferably from 30 to 50% by weight during the reduction reaction.

In another embodiment of the present invention, the evaporation ratio of the starting materials of an alcohol of 20% by weight or more is preferred for the following reasons:

When the liquid phase reaction is dominant in the hydrogenation in the reduction reactor, since an insufficient amount of hydrogen is dissolved in the starting materials of an alcohol constituting the liquid phase in the reaction system, the reaction activity is decreased, and a sufficient shifting effect of the reaction equilibrium cannot be expected in the gas phase reaction. Therefore, the unreacted starting materials and the wax ester formed as the reaction intermediate are liable to remain in the resulting alcohol. When the conditions are satisfactorily met, sufficient to give an evaporation ratio is 20% by weight or more, however, the hydrogenation reaction in the gas phase reaction is effectively conducted. Additionally, the amounts of the unreacted starting materials and the wax ester can be further decreased because the reaction equilibrium of the liquid phase shifts toward the alcohol side owing to the transformation of the resulting alcohol into the gas phase.

Further, in another embodiment of the present invention, the evaporation ratio of the starting materials of an alcohol of less than 60% by weight is preferred for the following reasons:

When the conditions are satisfactorily met, sufficient to give an evaporation ratio of the starting materials of an alcohol of 60% by weight or more, the resulting alcohol has high quality as described above. However, a large amount of a hydrogen gas is necessary for the reaction, which can lead to a large scale of the reduction reactor and other equipments such as pipe arrangements. When the conditions are satisfactorily, sufficient to give an evaporation ratio of less than 60% by weight, however, the necessary amount of a hydrogen gas can be decreased by adjusting the molar ratio of hydrogen, thereby the scale of the equipment can be made small. Furthermore, since a flow rate, a linear rate in particular, of the vapor of the starting materials of an alcohol through the catalytic layer can be decreased, the unreacted starting materials can be prevented from flowing through the catalytic layer without being subjected to reduction reaction.

In another embodiment, in order to achieve the evaporation ratio of the starting materials of an alcohol within the above-mentioned range, the reaction conditions such as a temperature, a pressure and a molar ratio of hydrogen are suitably adjusted as follows:

As for the temperature and pressure conditions, they may more preferably satisfy a temperature inside the reduction reactor in the range of from 100 to 300° C. and a pressure inside the reduction reactor in the range of from 10 and 100 atm. Particularly suitable pressure and temperature condition ranges are a pressure of from 20 to 60 atm. and a temperature of from 150 to 270° C. A pressure of 10 atm. or more is preferred from the viewpoint of keeping the reaction speed and shifting the reaction equilibrium toward the product side. A pressure of 100 atm. or less is preferred from the viewpoint of easily vaporizing the starting materials of an alcohol at this pressure and preventing increase in costs for the equipments and in the maintenance costs owing to higher pressures. In addition, a temperature of 100° C. or more is preferred from the viewpoint of keeping the reaction speed and easily vaporizing the starting materials of an alcohol, and a temperature of 300° C. or less is preferred from the viewpoint of the selectivity of the resulting alcohol.

In the case where a mixture of fatty acid methyl esters listed in Table 1, for example, is used as the starting materials of an alcohol, the molar ratio of hydrogen is preferably in the range of from 20 to 600, and more preferably in the range of from 50 to 500. A molar ratio of hydrogen of 20 or more is preferred from the viewpoint of keeping the reaction speed and decreasing the amount of the unreacted starting materials remaining in the resulting alcohol. A molar ratio of hydrogen of 600 or less is preferred from the viewpoint of decreasing the amount of the unreacted starting materials remaining in the resulting alcohol owing to the fact that the unreacted starting materials are prevented from flowing through the catalytic layer without being subjected to reduction reaction caused by a high flow rate of the vaporized starting materials in the reaction system by having a large molar ratio of hydrogen. Alternatively, in the case where, for example, lauric acid is used as a starting material of an alcohol, the molar ratio of hydrogen is preferably in the range of from 20 to 600, and more preferably in the range of from 20 to 500.

In another embodiment, since the necessary amount of a hydrogen gas in the reduction can be decreased, the running cost can be remarkably lowered. At the same time, the reduction reactor and the other equipments such as pipe arrangements can be made compact, which thereby leads to the decrease of the equipment investment, making it economically advantageous.

By the adjustment of the reaction conditions within the above-mentioned ranges, the amounts of hydrocarbons formed as the by-products and the unreacted starting materials of an alcohol included in alcohol at the outlet of the reactor can be decreased, and additionally, the wax ester formed as the reaction intermediate can be selectively allowed to remain in the resulting alcohol. Since the wax ester has a boiling point region largely different from that of the alcohol obtained as the primary product, the wax ester can be easily separated by distillation, and the recovered wax ester can be fed to the reduction reactor again as a starting material for the hydrogenation reaction, and thus providing economically advantageous process.

As described above, according to the method of the present invention, alcohols having good quality which include only small amounts of hydrocarbons and wax esters can be produced. Even when the evaporation ratio of the starting materials of an alcohol is decreased from an economical point of view, the production method is remarkably industrially advantageous because the wax ester which can be easily separated can be selectively allowed to remain in resulting alcohol.

The present invention will be explained in further detail by means of the following working Examples and Comparative Examples, but the present invention is not restricted to these Examples.

EXAMPLES 1 THROUGH 9 AND COMPARATIVE EXAMPLES 1 THROUGH 5

A reaction tower with an inner diameter of 25 mm$\phi$ and a height of 2 m was packed with 500 cc of a Cu—Cr catalyst ("N202D" manufactured by NIKKI CHEMICAL Co., Ltd.) formed in a rod shape with a diameter of 3 mm$\phi$, and the catalyst was reduced to be activated. Thereafter, a mixture of a fatty acid methyl ester including a fatty acid moiety with 8 to 18 carbon atoms was subjected to a hydrogenation reaction by continuously flowing the mixture through the tower together with a hydrogen gas. The reaction conditions and found values obtained in each of Examples and Comparative Examples are listed in Tables 2 and 3. The composition of the mixture of the fatty acid methyl esters is listed in Table 1.

In each of Examples and Comparative Examples, the amounts of the wax ester and the hydrocarbon were quantitatively obtained by diluting a sample collected at the outlet of the reaction tower with a solvent and analyzing the sample by capillary gas chromatography.

TABLE 2

| | Example Nos. | | | | | | |
|---|---|---|---|---|---|---|---|
| | 1 | 2 | 3 | 4 | 5 | 6 | 7 |
| Reaction Pressure (atm) | 70 | 50 | 40 | 40 | 60 | 50 | 50 |
| Reaction Temperature (° C.) | 200 | 200 | 200 | 200 | 220 | 220 | 220 |
| Molar Ratio of Hydrogen | 80/1 | 100/1 | 100/1 | 150/1 | 200/1 | 400/1 | 50/1 |
| Evaporation Ratio (% by wt) | 23 | 32 | 42 | 51 | 61 | 77 | 28 |
| L H S V (1/hr) | 0.50 | 0.50 | 0.50 | 0.50 | 0.50 | 0.50 | 0.50 |
| Unreacted Ester (% by wt) | 0.10 | 0.08 | 0.06 | 0.10 | 0.10 | 0.18 | 0.12 |
| Wax Ester (% by wt) | 3.58 | 2.24 | 2.68 | 1.89 | 2.03 | 1.60 | 3.20 |
| Hydrocarbons (% by wt) | 0.04 | 0.05 | 0.06 | 0.08 | 0.10 | 0.11 | 0.07 |
| Velocity Ratio (VG/VL) | 203 | 400 | 583 | 1035 | 1212 | 4889 | 197 |

TABLE 3

|  | Example Nos. | | Comparative Example Nos. | | | | |
| --- | --- | --- | --- | --- | --- | --- | --- |
|  | 8 | 9 | 1 | 2 | 3 | 4 | 5 |
| Reaction Pressure (atm) | 50 | 50 | 80 | 50 | 40 | 20 | 50 |
| Reaction Temperature (° C.) | 220 | 220 | 200 | 220 | 220 | 220 | 220 |
| Molar Ratio of Hydrogen | 100/1 | 200/1 | 25/1 | 25/1 | 600/1 | 400/1 | 700/1 |
| Evaporation Ratio (% by wt) | 46 | 65 | 6 | 16 | 84 | 85 | 83 |
| L H S V (1/hr) | 0.50 | 0.50 | 0.50 | 0.50 | 0.50 | 0.50 | 0.50 |
| Unreacted Ester (% by wt) | 0.08 | 0.10 | 0.27 | 0.21 | 0.26 | 0.35 | 0.30 |
| Wax Ester (% by wt) | 2.33 | 1.96 | 7.36 | 5.22 | 0.38 | 0.93 | 0.83 |
| Hydrocarbons (% by wt) | 0.08 | 0.09 | 0.03 | 0.04 | 0.11 | 0.13 | 0.13 |
| Velocity Ratio (VG/VL) | 525 | 1620 | 46 | 84 | 13227 | 18004 | 11676 |

Figure 2:
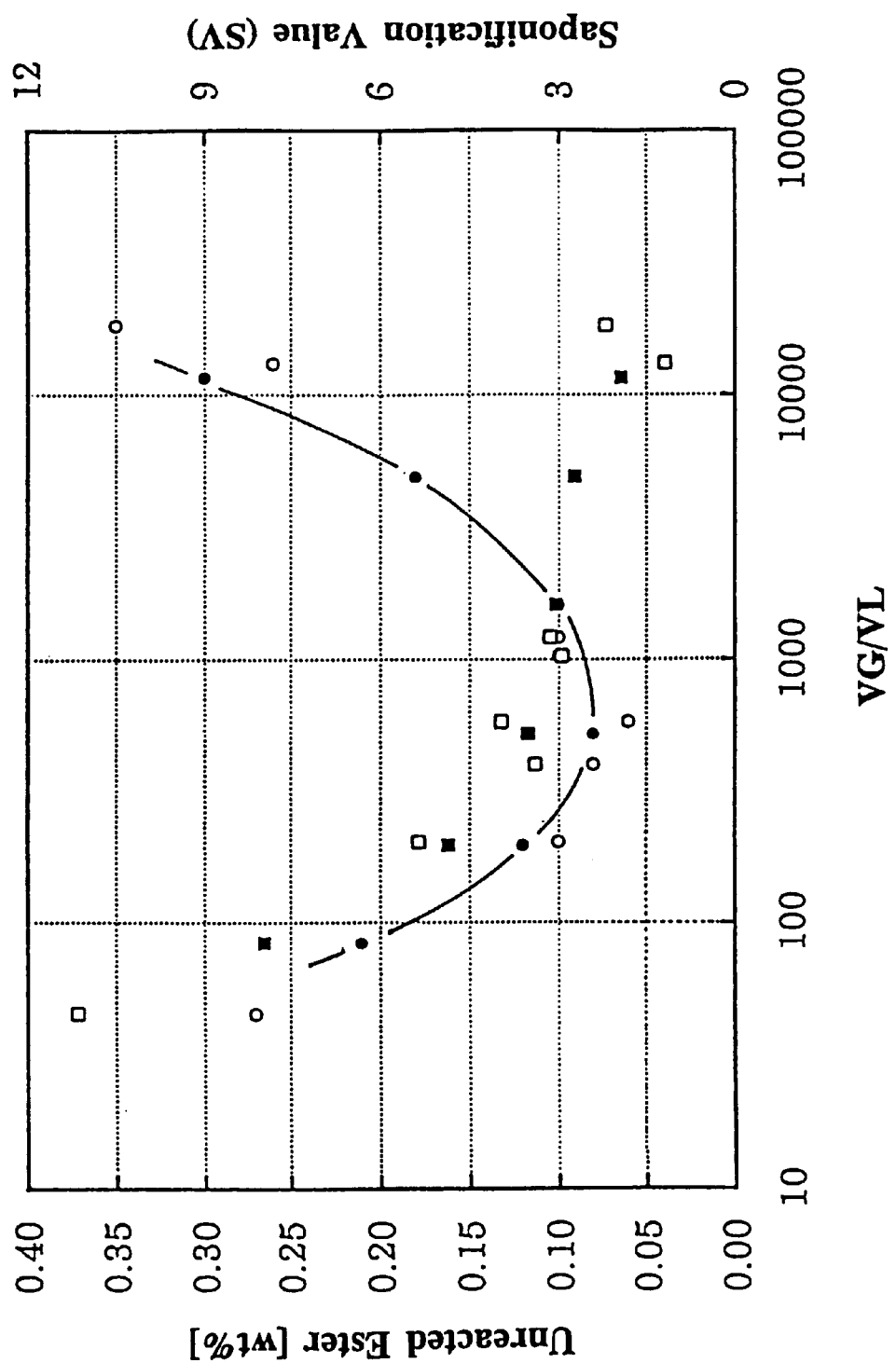
FIG. 2 is a graph showing the relationship between the superficial velocity ratio (VG/VL) and qualities of the resulting products, such as amounts of unreacted ester and saponification values, wherein □ and ■ indicate saponification values; and ○ and ● indicate the amounts of unreacted esters. Here, ■ and ● are data obtained under the conditions of 50 atm. and 220° C.

FIGS. 1 and 2 show the effects of the evaporation ratio and those of the linear flow rate of the starting materials of an alcohol on the quantity of the product in each of Examples and Comparative Examples. The saponification values (SV) shown in FIGS. 1 and 2 reflect the amounts of methyl ester and the wax ester remaining in the resulting alcohol, wherein the saponification values were measured in accordance with JIS K 0070 indicated as the amount (mg) of potassium hydroxide spent for saponifying one gram of the sample.

The term "LHSV" stands for "liquid hourly space velocity" which is a value obtained by dividing the volume flow rate of the starting materials per unit time by the volume of the reactor.

EXAMPLE 10

A similar hydrogenation reaction as above was carried out using the same reaction tower and catalyst as in Examples 1 to 9 except that lauric acid was used as a starting material of an alcohol. The reaction conditions and the found values of the resulting product are given below.

Starting material: Lauric acid;

Reaction pressure: 50 (atm.);

Reaction temperature: 220 (° C.);

Molar ratio of hydrogen: 200/1;

Evaporation ratio: 56 (% by weight);

LHSV: 0.15 (1/hr);

Unreacted starting materials: 0.09 (% by weight);

Wax ester: 3.13 (% by weight);

Hydrocarbons: 0.10 (% by weight); and

Velocity ratio (VG/VL): 1289.

Examples and Comparative Examples reveal the following:

In the cases of Comparative Examples 1 and 2 where the evaporation ratios of methyl ester in the reduction reactor are lower than 20% by weight, the amounts of unreacted ester included in the resulting alcohols are large, and the amounts of the wax ester formed as the reaction intermediate are also large for the following reasons. The effect of the gas phase reaction cannot be sufficiently obtained because the evaporation ratio is small at a low pressure, which give rise to a low reaction activity in the liquid phase. In the cases of Comparative Examples 3 to 5 where the evaporation ratios exceed 80% by weight, although the amount of wax ester was small owing to the effect of the gas phase reaction, the unreacted esters remain in the resulting alcohols because the flow rate at the gas phase portion through the catalytic layer is high. Since this unreacted ester is difficult to be separated from the resulting alcohol by distillation, the methods of these Comparative Examples are industrially disadvantageous. In order to decrease the amount of the unreacted ester, the LHSV needs to be made small. However, even when the LHSV is small, these methods are not economical because of their low productivity.

In Examples 1 through 9, the evaporation ratios of methyl ester are adjusted in the range of from 20 to 80% by weight, so that the amount of unreacted ester is made small. Such a small amount of unreacted ester is not needed to be separated from the resulting alcohol when the alcohol is used, for example, as a starting material for a detergent. Furthermore, although the amount of the wax ester formed in each of Examples is larger than those with the evaporation ratios exceeding 80% by weight, since the wax ester can be easily separated by distillation and recycled in the process, thereby posing no problems in the quality of the resulting alcohol. Also, FIGS. 1 and 2 reveal that the method of the present invention provides preferred reaction conditions from the viewpoint of the amount of unreacted ester and the saponification value.

Additionally, when a fatty acid is used as a starting material, an alcohol with a desirably high quality can be produced (Example 10).

INDUSTRIAL APPLICABILITY

In the method of the present invention, by suitably selecting an evaporation ratio of the starting materials of an alcohol, it is possible to produce an alcohol wherein the amounts of such components as unreacted starting materials of alcohols, wax esters formed as reaction intermediates, and hydrocarbons formed as by-products are remarkably lowered to such an extent that a purification step, such as distillation, is not necessitated. In addition, even when the reaction pressure is low, particular wax esters formed as reaction intermediates are selectively kept in the reaction system, so that subsequent processes are made easy, thereby making it economically advantageous.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for producing an alcohol comprising the steps of:

continuously feeding starting materials of an alcohol; and carrying out catalytic reduction reaction of the starting materials in the presence of a hydrogenation catalyst, wherein said starting materials of an alcohol and a hydrogen gas are fed in a gaseous state or a mixture of liquid and gaseous states in a reduction reactor, and wherein said catalytic reduction reaction of the starting materials is carried out under temperature conditions, pressure conditions, and conditions of a molar ratio of hydrogen ((hydrogen molecules/(acyl groups in the starting materials)), sufficient to give an evaporation ratio of the starting materials of from 20 to 80% by weight, and wherein a ratio of VG to VL satisfies the following relationship in the reduction reactor:

$$100 \leq VG/VL \leq 10000,$$

wherein "VG" stands for the superficial velocity at a gas phase portion of a mixture of the starting materials of an alcohol fed and a hydrogen gas; and "VL" stands for the superficial velocity at a liquid phase portion of said mixture.

2. The method according to claim 1, wherein said starting materials of an alcohol are a fatty acid ester or a fatty acid.

3. The method according to claim 2, wherein said fatty acid ester or the fatty acid is derived from coconut oil, palm oil, or palm kernel oil.

4. The method according to claim 1, wherein the evaporation ratio of the starting materials of an alcohol is 20% by weight or more and less than 60% by weight in the reduction reaction.

5. The method according to claim 1, wherein the evaporation ratio of the starting materials of an alcohol is from 60 to 80% by weight in the reduction reaction.

6. The method according to claim 1, wherein a fixed bed reactor containing a hydrogenation catalyst fixed inside the reactor is used as the reduction reactor.

7. The method according to claim 1, wherein the temperature inside the reduction reactor is from 100 to 300° C., and the pressure inside the reduction reactor is from 10 to 100 atm.

* * * * *